(12) United States Patent
Lee

(10) Patent No.: US 8,075,533 B2
(45) Date of Patent: Dec. 13, 2011

(54) AUTOFLUSH SYRINGE

(75) Inventor: Martin Nicholas Lee, Davis, CA (US)

(73) Assignee: Preventiv, Inc., Menlo Park, CA (US)

( * ) Notice: Subject to any disclaimer, the term of this patent is extended or adjusted under 35 U.S.C. 154(b) by 1616 days.

(21) Appl. No.: 11/120,906

(22) Filed: May 2, 2005

(65) Prior Publication Data

US 2006/0258977 A1 Nov. 16, 2006

(51) Int. Cl.
*A61M 5/00* (2006.01)
*A61M 5/315* (2006.01)

(52) U.S. Cl. ......................... 604/191; 604/220

(58) Field of Classification Search .................. 604/82, 604/87, 88, 90, 187, 191, 198, 263, 218, 604/220, 246, 271
See application file for complete search history.

(56) References Cited

U.S. PATENT DOCUMENTS

| | | | |
|---|---|---|---|
| 368,627 A | 8/1887 | Threlfall | |
| 553,234 A | 1/1896 | Finot | |
| 1,142,682 A * | 6/1915 | Dickinson | 604/220 |
| 1,234,582 A * | 7/1917 | Trueblood | 604/191 |
| 1,343,787 A * | 6/1920 | Ewell | 604/220 |
| 2,841,145 A | 7/1958 | Epps | |
| 3,559,645 A | 2/1971 | Schaller | |
| 3,605,742 A * | 9/1971 | Tibbs | 604/112 |
| 3,705,582 A | 12/1972 | Stumpf et al. | |
| 3,729,031 A | 4/1973 | Baldwin | |
| 3,747,812 A | 7/1973 | Karman et al. | |
| 3,835,835 A * | 9/1974 | Thompson et al. | 600/575 |
| 3,923,058 A * | 12/1975 | Weingarten | 604/191 |
| 4,171,698 A | 10/1979 | Genese | |
| 4,188,949 A * | 2/1980 | Antoshkiw | 604/191 |
| 4,313,439 A | 2/1982 | Babb et al. | |
| 4,411,157 A | 10/1983 | Babin et al. | |
| 4,452,473 A | 6/1984 | Ruschke | |
| 4,476,866 A * | 10/1984 | Chin | 606/194 |
| 4,501,306 A | 2/1985 | Chu et al. | |
| 4,506,691 A | 3/1985 | Tseo | |
| 4,562,844 A * | 1/1986 | Carpenter et al. | 600/488 |
| 4,581,015 A | 4/1986 | Alfano | |
| 4,583,978 A | 4/1986 | Porat et al. | |
| 4,655,747 A | 4/1987 | Allen, Jr. | |
| 4,685,910 A * | 8/1987 | Schweizer | 604/218 |
| 4,693,706 A * | 9/1987 | Ennis, III | 604/87 |
| 4,702,737 A * | 10/1987 | Pizzino | 604/191 |
| 4,715,853 A | 12/1987 | Prindle | |
| 4,723,943 A * | 2/1988 | Spencer | 604/198 |

(Continued)

OTHER PUBLICATIONS

Lee, Martin N.; U.S. Appl. No. 12/833,735 entitled 'Autoflush syringe, filed Jul. 9, 2010.

(Continued)

*Primary Examiner* — Jackie Ho
*Assistant Examiner* — William Carpenter
(74) *Attorney, Agent, or Firm* — Levine Bagade Han LLP

(57) ABSTRACT

A two-chambered, sequentially injectable syringe is disclosed. The syringe has two concentric barrels, substantially cylindrical in shape. The outer barrel has an open end adapted for receiving an inner barrel/first piston. The inner barrel/first piston contains a flushing liquid. The syringe has a second piston slidably movable in the inner barrel and a latching mechanism that can alternate between a locked configuration and an unlocked configuration. In the locked configuration, the latching mechanism prevents the second piston from substantially all longitudinal movement relative to the inner barrel. In the unlocked configuration, the latching mechanism permits longitudinal motion of the second piston within the inner barrel.

10 Claims, 10 Drawing Sheets

U.S. PATENT DOCUMENTS

| | | | |
|---|---|---|---|
| 4,747,834 A | | 5/1988 | Prindle |
| 4,758,232 A | * | 7/1988 | Chak ............................ 604/220 |
| 4,871,353 A | | 10/1989 | Thomsen |
| 4,874,385 A | * | 10/1989 | Moran et al. ................... 604/208 |
| 4,929,230 A | | 5/1990 | Pfleger |
| 4,929,238 A | | 5/1990 | Baum |
| 4,950,241 A | | 8/1990 | Ranford |
| 4,986,813 A | | 1/1991 | Blake, III et al. |
| 5,032,117 A | * | 7/1991 | Motta ............................ 604/88 |
| 5,358,497 A | * | 10/1994 | Dorsey et al. ................. 604/220 |
| 5,374,250 A | | 12/1994 | Dixon |
| 5,435,076 A | | 7/1995 | Hjertman et al. |
| 5,496,284 A | | 3/1996 | Waldenburg |
| 5,512,054 A | | 4/1996 | Morningstar |
| 5,720,731 A | | 2/1998 | Aramata et al. |
| 5,772,433 A | | 6/1998 | Esrock |
| 5,772,630 A | | 6/1998 | Ljungquist |
| 5,833,654 A | | 11/1998 | Powers et al. |
| 6,090,077 A | | 7/2000 | Shaw |
| 6,270,482 B1 | | 8/2001 | Rosoff et al. |
| 6,361,524 B1 | | 3/2002 | Odell et al. |
| 6,423,050 B1 | | 7/2002 | Twardowski |
| 6,558,358 B2 | | 5/2003 | Rosoff et al. |
| 6,719,733 B1 | | 4/2004 | Heffernan et al. |
| 6,723,074 B1 | | 4/2004 | Halseth |
| 6,780,167 B2 | | 8/2004 | Leone |
| 6,866,653 B2 | | 3/2005 | Bae |
| 6,972,005 B2 | | 12/2005 | Boehm, Jr. et al. |
| 6,997,910 B2 | | 2/2006 | Howlett et al. |
| 7,011,650 B2 | | 3/2006 | Rosoff et al. |
| 7,041,084 B2 | | 5/2006 | Fojtik |
| 7,048,720 B1 | | 5/2006 | Thorne, Jr. et al. |
| 7,101,354 B2 | | 9/2006 | Thorne, Jr. et al. |
| 7,204,797 B2 | | 4/2007 | Reilly et al. |
| 2002/0022807 A1 | | 2/2002 | Duchon et al. |
| 2002/0035351 A1 | | 3/2002 | Lodice |
| 2002/0128609 A1 | * | 9/2002 | Koch et al. ..................... 604/218 |
| 2002/0197211 A1 | | 12/2002 | Henriksen et al. |
| 2003/0009132 A1 | | 1/2003 | Schwartz et al. |
| 2003/0040712 A1 | | 2/2003 | Ray et al. |
| 2003/0199816 A1 | | 10/2003 | Ramming |
| 2003/0212371 A1 | | 11/2003 | Smith et al. |
| 2003/0213504 A1 | | 11/2003 | Cerra et al. |
| 2004/0039346 A1 | | 2/2004 | Baldwin et al. |
| 2004/0097875 A1 | * | 5/2004 | Bae ................................ 604/89 |
| 2004/0116871 A1 | | 6/2004 | Vincent |
| 2005/0065479 A1 | | 3/2005 | Schiller et al. |
| 2005/0081914 A1 | | 4/2005 | Kalley et al. |
| 2006/0030816 A1 | | 2/2006 | Zubry |
| 2006/0100591 A1 | | 5/2006 | Alheidt et al. |
| 2006/0173415 A1 | | 8/2006 | Cummins |
| 2006/0258977 A1 | | 11/2006 | Lee |
| 2007/0249996 A1 | | 10/2007 | Tennican et al. |
| 2007/0265574 A1 | | 11/2007 | Tennican et al. |
| 2008/0114304 A1 | | 5/2008 | Nalesso et al. |
| 2008/0119782 A1 | | 5/2008 | Steinman et al. |
| 2008/0119794 A1 | | 5/2008 | Alheidt et al. |
| 2009/0287184 A1 | | 11/2009 | Lee |

OTHER PUBLICATIONS

Lee et al.; U.S. Appl. No. 12/847,825 entitled 'Two chamber syringe with locking mechanism, filed Jul. 30, 2010.

* cited by examiner

FIG. 1
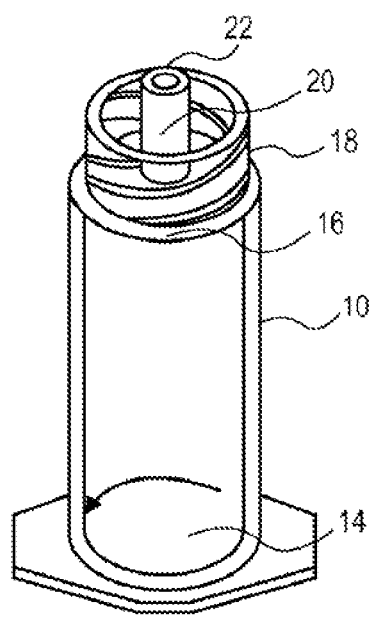
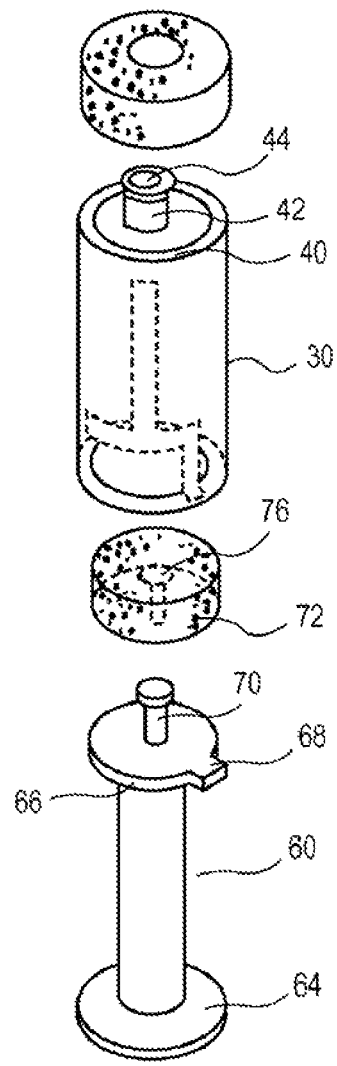

FIG. 2
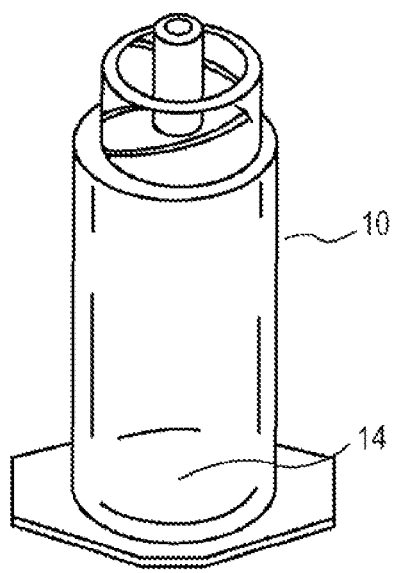
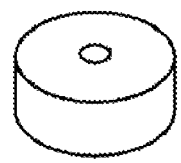
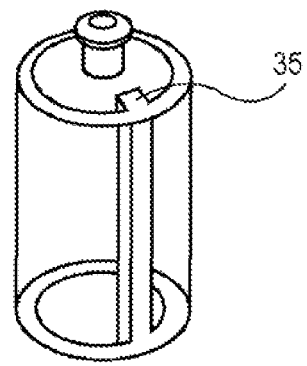
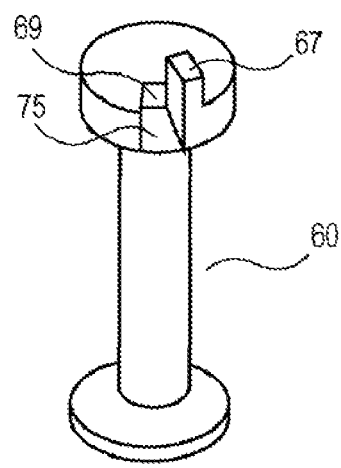

FIG. 7 FIG. 8
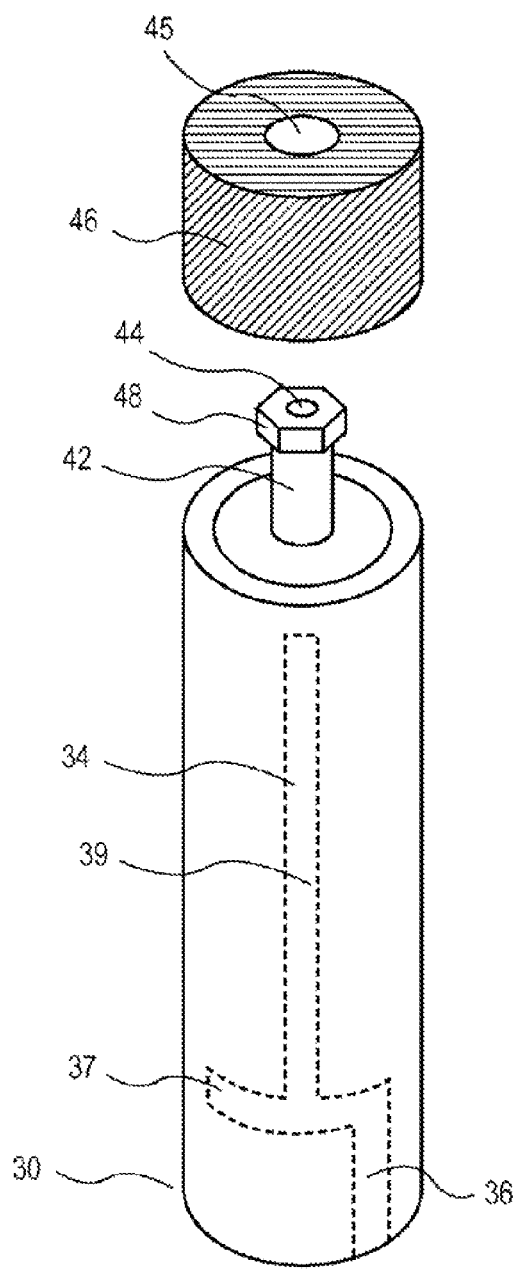
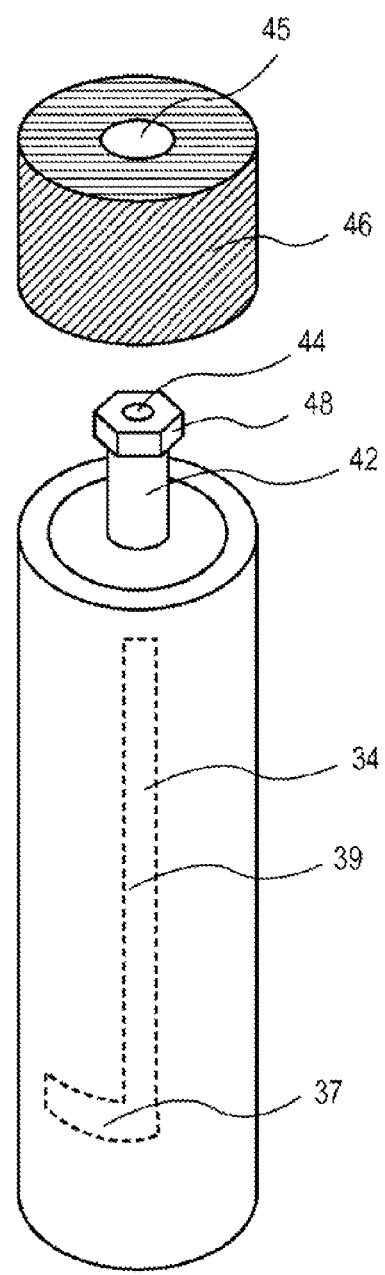

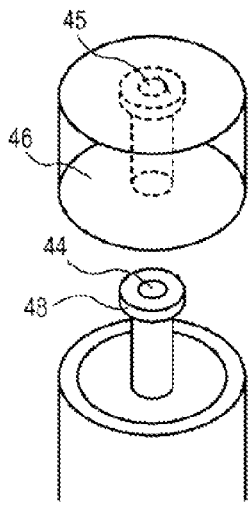
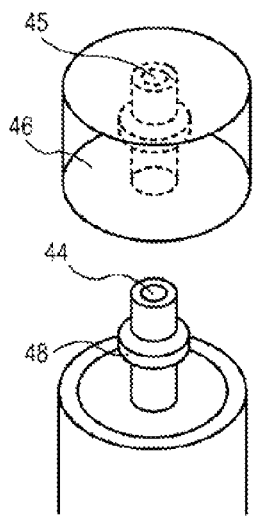
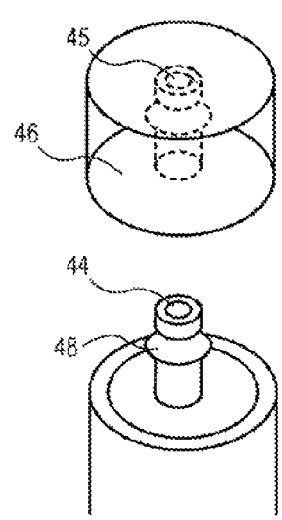
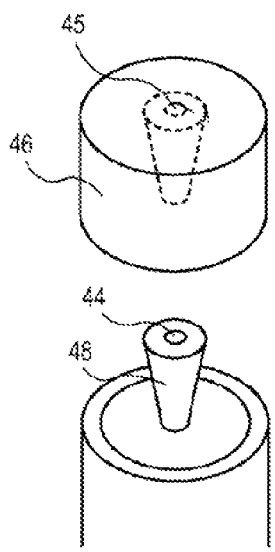
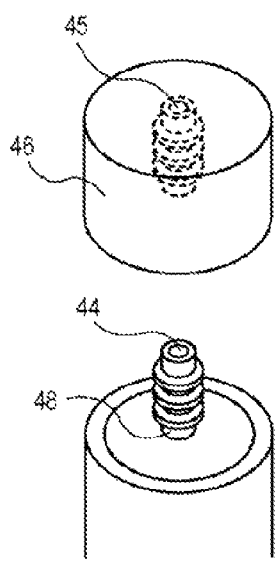
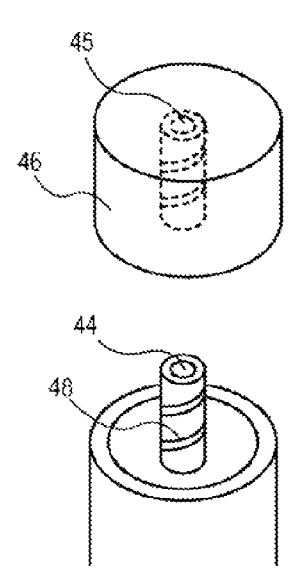

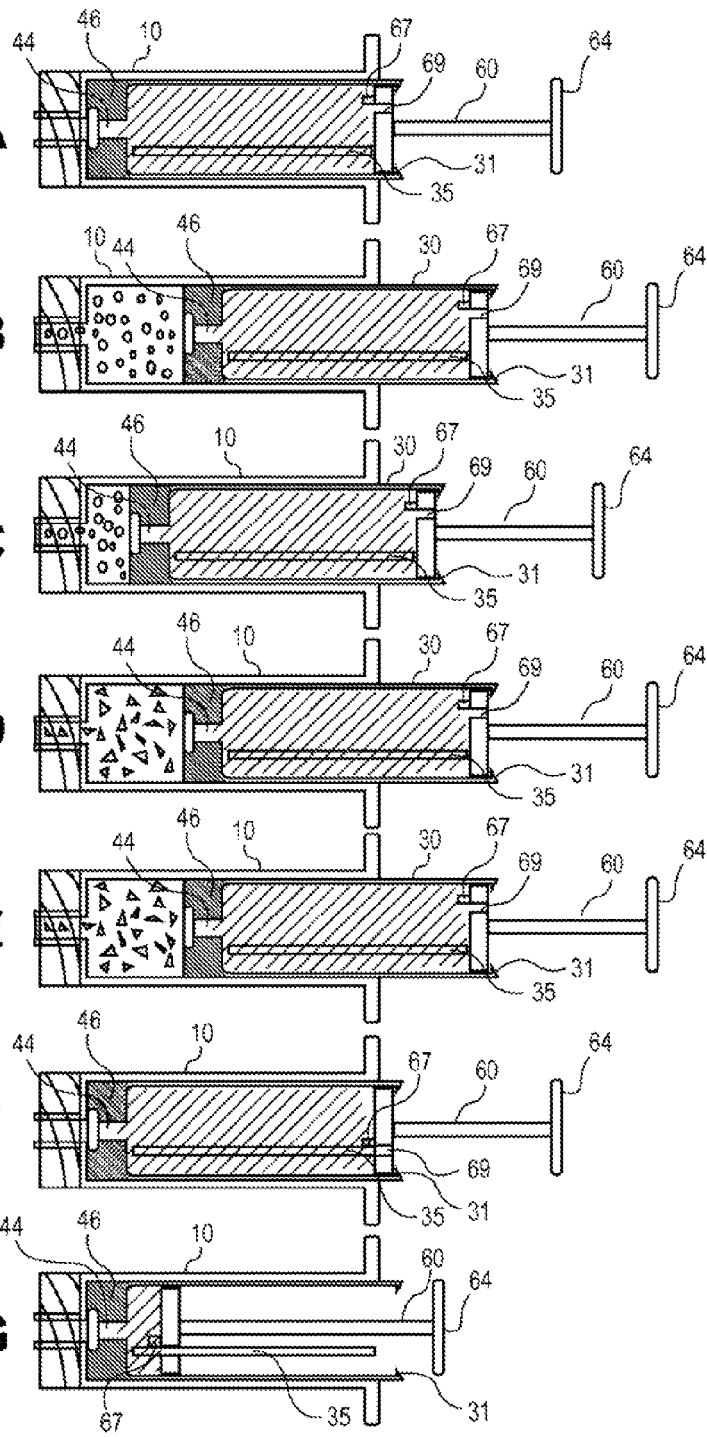

AUTOFLUSH SYRINGE

BACKGROUND OF THE INVENTION

1. Field of the Invention

This invention relates to syringe injectors.

2. General Background

Syringes are commonly used in the medical field for the injection or withdrawal of liquid medications. Syringes typically have a hollow glass or plastic barrel with an internal piston. By moving the piston, a user can create a positive or negative pressure inside the barrel, thereby transmitting fluid out of or into the barrel through a small opening opposite the piston.

Syringes are often used in intravenous therapy where the syringe may directly puncture the vein, or more commonly, may be used in conjunction with a catheter. When a catheter is used, one side of the catheter remains in the vein, while the other side remains outside the skin. The external portion of the catheter typically includes a coupler for connection to a syringe.

After injection in either procedure, a small amount of medication is typically left behind. When a syringe is used, the medication remains within the tip of the syringe. When a catheter is used in conjunction with a syringe, the unadministered medication remains in the both the tip of the syringe and in the catheter.

This leftover medication is problematic for several reasons. First, it necessarily means that the entire amount of medicine drawn into the syringe does not reach the patient. Second, many medications are time sensitive and should not remain in the catheter until a subsequent medicine flushes it through.

In a catheter system, these problems are solved using a second liquid to immediately flush the remaining medication out of the catheter and into the patient. Generally, a second syringe prefilled with a flushing solution provides the second liquid.

While many different liquids may be used to flush the catheter, the most commonly used liquid is a 0.9% concentration of sodium chloride (saline solution). The saline solution is injected from a syringe into the catheter, thereby flushing any stranded medication into the patient. Thus, the saline flush ensures that a full dosage of medication has been timely delivered.

This method for purging the catheter has certain disadvantages. For instance, by using a separate syringe for each injection, there is an increased chance of medical error. Most medicines are colorless (like the saline solution), and it is easy to accidentally administer medication when intending to flush the line or vice versa. This risk is increased when clinicians carry medicines for multiple patients at one time.

The likelihood of error is compounded in an emergency, when it may be necessary to inject several medications quickly and in a specific order. In such situations, a separate saline flush is necessary between every individual medication injection, so the risk of error is high, and the consequences of a mistake may be grave.

Finally, the clinician may be distracted by a separate medical need during the time between the injection of medication and the saline flush. Without some reminder, the clinician may forget that he or she has not flushed the line.

Even if all precautions are taken and the two injections are made in the proper order, drawbacks remain. With each breach of the catheter's seal for injection, the patient is potentially exposed to bacteria, increasing the risk of infection. By requiring a clinician to access the system once for the medication and a second time for the flush, the risk of infection is doubled.

Using a second syringe for the saline flush also wastes resources. Attaching a second syringe to the catheter takes time, and since a clinician may perform a saline flush more than one hundred times per day, this lost time adds up quickly. Finally, requiring a second syringe unnecessarily increases the already significant costs related to manufacturing, shipping, storage, and disposal of syringes.

The present invention advances the state of the art by providing a cost-effective single syringe that both administers medication and flushes the intravenous system. By using a single syringe for both purposes, a clinician need only access the intravenous catheter once, thereby decreasing the rate of error and infection. Additionally, the presence of the saline or other solution in the syringe after injection alerts the clinician of the need to flush the system, thus reducing the chance that the flush would be forgotten. Finally, the extra cost and time associated with a second "flush-only" syringe would be eliminated.

The applicant's invention solves all of these problems, and does so with a simple design that makes storage easy and keeps manufacturing costs to a minimum.

SUMMARY OF THE INVENTION

The present invention is a two-chambered syringe with an outer barrel having an open end for slidably receiving an inner barrel/first piston. A second piston is slidably movable in the inner barrel/first piston. A latching mechanism locks and unlocks the inner barrel/first piston to the second piston. In the locked configuration, the second piston is prevented from substantially all longitudinal movement relative to the inner barrel/first piston, and in the unlocked configuration, the second piston may move longitudinally within the inner barrel. Thus, the invention may be repeatedly used as a traditional syringe to withdraw medicine from a bottle, either before or after the administration of a second flushing solution contained in the syringe.

BRIEF DESCRIPTION OF THE DRAWINGS

FIG. 1 is an exploded perspective view of a two-chambered syringe according to an embodiment of the present invention.

FIG. 2 is an exploded perspective view of a two-chambered syringe according to an embodiment of the present invention.

FIG. 7 is a perspective view of the inner barrel/first piston and sealing ring depicted in FIG. 1.

FIG. 8 is a perspective view of the inner barrel/first piston and sealing ring according to an alternative embodiment of the present invention.

FIGS. 9-14 are perspective views of the proximal end of the second piston and sealing ring according to alternative embodiments of the present invention.

FIGS. 15(a)-(g) are side cross-sectional views of various stages of operation of the two-chambered syringe depicted in FIG. 1.

DETAILED DESCRIPTION

Figure 3:
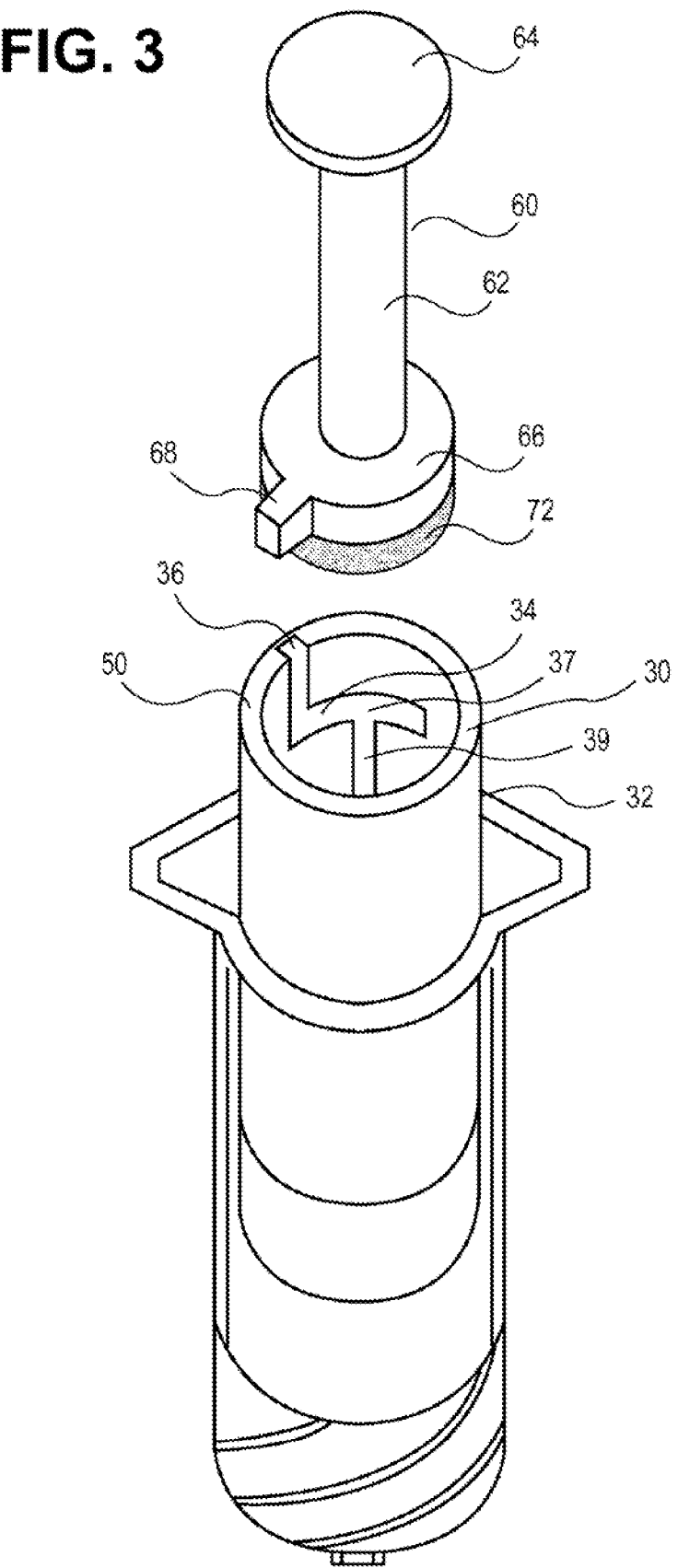
FIG. 3 is a perspective view of the embodiment depicted in FIG. 1.

The present invention is a two-chambered syringe with three basic components: (i) an outer barrel 10 for holding a first liquid 26, (ii) an inner barrel/first piston 30 for holding a flushing liquid 52, and (iii) a second piston 60. See FIG. 5. The syringe also includes a latching mechanism for controlling the movement of the second piston 60 in the inner barrel/first piston 30. See FIGS. 3 and 4.

The barrels and pistons may be constructed of polypropylene or other similar inert, nonreactive semi-flexible material. Both barrels 10, 30 are generally circular cylinders. The inner barrel/first piston 30 acts as both a barrel and a piston. That is, it both holds liquid like a barrel, and may be used as a plunger to expel liquid from the outer barrel 10. See FIGS. 5 and 6.

For purposes of this patent, the proximal end of the syringe is the end typically comprising a first conduit 20, while the distal end is the end of the syringe typically comprising the second piston 60 and a gripping handle 64. See FIGS. 1 and 2.

The outer barrel 10 has an outer barrel distal open end 14 adapted for receiving the inner barrel/first piston 30. See FIG. 1. The inner barrel/first piston 30 is slidably contained in outer barrel 10 in a liquid-tight relation, similar to the piston or plunger in syringes common to the art. See FIGS. 1-6 and 15.

In one embodiment, a proximal end 16 of the outer barrel 10 may comprise an adapter 18, such as a luer connector device as disclosed in U.S. Pat. No. 4,452,473, or other locking means common in the art. See FIG. 1. The adapter 18 allows a connection between the present invention and an intravenous system. An outer barrel open proximal end 22 is at the proximal end 16 of the outer barrel 10 and may contain a first conduit 20. See FIG. 1. The distal end of first conduit 20 is in communication with the proximal end 16 of the outer barrel 10, providing a passageway for fluid from either the outer barrel 10 or the inner barrel/first piston 30. See FIG. 1.

The inner barrel/first piston 30 has an inner barrel/first piston proximal end 40 slidably received within the outer barrel open distal end 14. See FIG. 1. It also includes a hollow projection 42 that extends proximally out of the inner barrel/first piston 30. See FIGS. 1, 9-14. The hollow projection 42 defines a second conduit 44 through which liquid flows from the inner barrel/first piston 30 to the outer barrel 10. See FIGS. 1 and 6-8. The hollow projection 42 has a flared tip 48 that secures a first sealing ring 46, as shown in FIGS. 7 and 8. The flared tip 48 may take many different forms, as shown in FIGS. 9-14.

The first sealing ring 46 comprises a sealing ring conduit 45 through which extends the hollow projection 42. See FIGS. 7-14. The first sealing ring 46 is substantially the same diameter as both the inner barrel/first piston outer wall 32 and the outer barrel inner wall 24, creating a liquid tight seal between the inner barrel/first piston 30 and the outer barrel 10. See FIG. 6. Thus, the only fluid connection between the inner barrel/first piston 30 and the outer barrel 10 is through the second conduit 44 and the sealing ring conduit 45. Id. The sealing ring 46 may be constructed of an elastic material such as natural or synthetic rubber.

The flushing liquid 52 is inside the inner barrel/first piston 30. See FIGS. 5, 5-6. The flushing liquid 52 may be a saline solution, or any other suitable solution, such as heparin, when anticoagulation is desired, or antibiotics, when a line infection is being treated.

The flushing liquid 52 occupies substantially all of the space defined by the inner barrel/first piston inner wall 50, and initially extends partially through the second conduit 44 defined by the hollow projection 42. See FIGS. 5 and 15. Because the flushing liquid 52 only extends partially through the second conduit 44, the flushing liquid 52 remains isolated from any liquid later drawn into the outer barrel 10. Id.

Figure 17A:
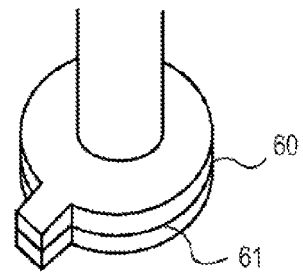
FIGS. 17(a) and (b) are perspective views of a portion of the inner barrel of a two-chambered syringe according to an embodiment of the present invention.
Figure 17B:
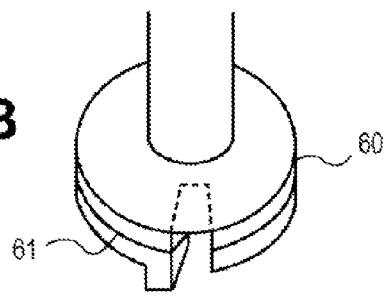

The second piston 60 is slidably placed within the inner barrel/first piston 30. See FIGS. 3-5 and 15. The second piston 60 comprises a second piston proximal end 66 further comprising a solid projection 70 that fits through an aperture 76 in a second sealing ring 72, thereby attaching the second piston 60 to the second sealing ring 72. See FIGS. 1, 3. The second sealing ring 72 is of substantially equal diameter to the inner barrel/first piston inner wall 50, and is created from an elastic rubber-like material that provides a liquid-tight seal for the inner barrel/first piston 30. See FIG. 3. Alternatively, this liquid-tight seal may be created by a similar rubber-like sealing material 61 placed around the periphery of the proximal end of the second piston 60. See FIG. 17. The second piston 60 moves in and out of the lumen of inner barrel/first piston 30, thereby dispensing liquid from or drawing liquid into the inner barrel/first piston 30. See FIG. 3.

Extending distally from second piston proximal end 66 is a piston rod 62. See FIGS. 3 and 4. A gripping handle 64 is placed at the most distal end of the second piston 60. Id.

The two-chambered syringe further comprises a latching mechanism that can alternate between an unlocked configuration and a locked configuration. See generally FIGS. 3-4 and 7-8. In the locked configuration, the second piston 60 is longitudinally locked relative to the inner barrel/first piston 30. See FIG. 15(b). In this configuration, the second piston 60 will not move longitudinally relative to the inner barrel/first piston 30. See FIGS. 5 and 15(a)-15(e). However, a longitudinal force applied to the second piston 60 will be transferred proximally and the inner barrel/first piston 30 will move relative to the outer barrel 10. Id.

In the unlocked configuration, the second piston 60 is free to move longitudinally relative to the inner barrel/first piston 30. See FIGS. 6 and 15(f)-15(g). Thus, the contents of the inner barrel/first piston 30 are ejected through the second conduit 44 when the second piston 60 is depressed. Id. When the second piston 60 is retracted, the inner barrel/first piston 30 will provide sufficient suction to draw in the contents of the outer barrel 10 through the second conduit 44.

Figure 4:
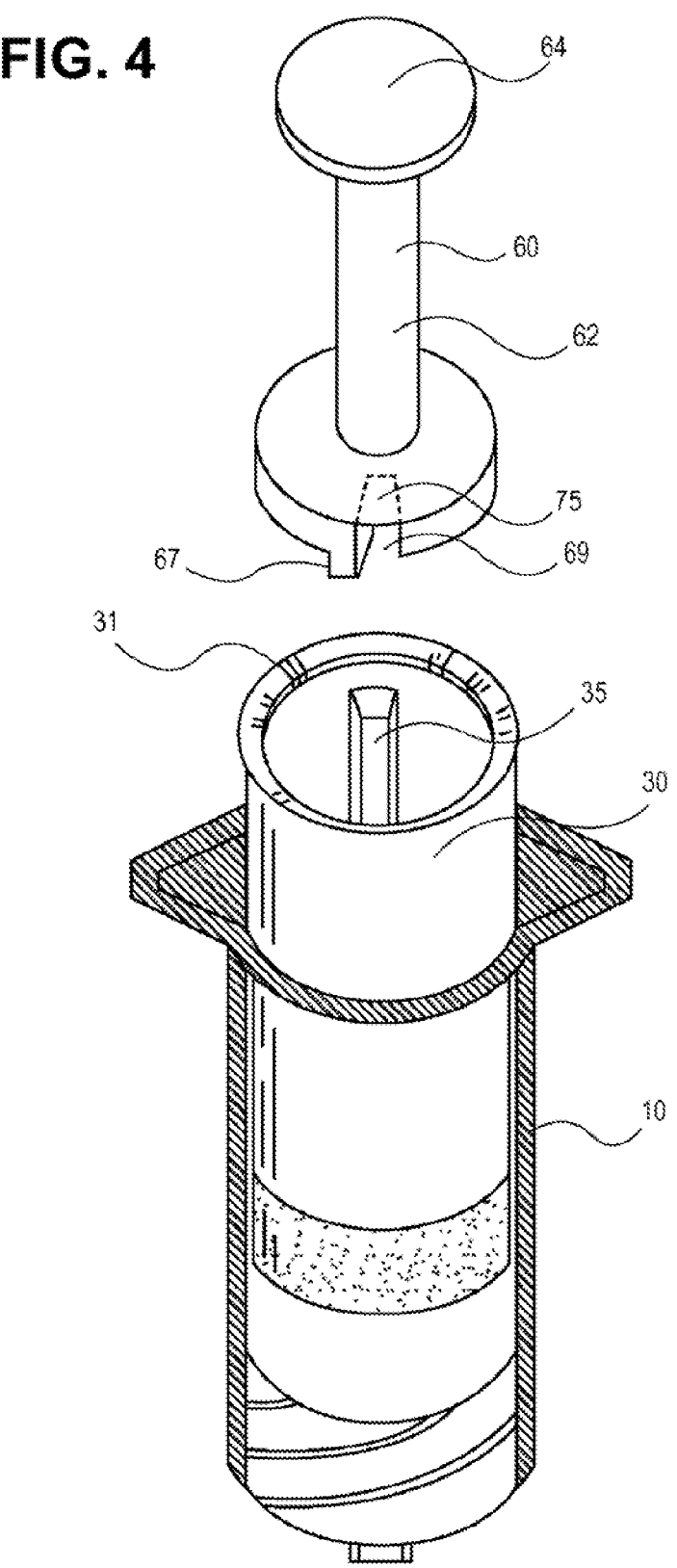
FIG. 4 is a perspective view of the embodiment depicted in FIG. 2.

In one embodiment, the latching mechanism comprises a projection 68, extending outward radially from near the second piston proximal end 66. See FIGS. 1 and 3. In this embodiment, the projection is constructed of a polypropylene or other similar inert, nonreactive semi-flexible material the same as or similar to that comprising the barrels and pistons of the syringe. While the radial width of the projection 68 shown in FIGS. 1 and 3 is small relative to the distance around piston rod 62, the same principle preventing movement of the piston rod 62 would apply regardless of the radial width or shape of projection 68. See FIG. 3.

This projection fits snugly into a groove 34 cut into the inner barrel/first piston inner wall 50, thereby allowing the second piston 60 to only move according a path of movement defined by groove 34. See FIGS. 3 and 6.

The groove 34 includes a longitudinal portion 39 extending longitudinally along the inner barrel/first piston inner wall 50, ending at the inner barrel/first piston proximal end 40. See FIG. 6. Near the distal end of the inner barrel/first piston 30, the longitudinal portion 39 makes a substantially right angle and continues circumferentially around the inner barrel/first piston inner wall 50 as a radial portion 37. See FIGS. 3, 6, and 8. In one embodiment, the radial portion 37 of the groove 34 extends less than one half of one revolution of the perimeter around the inner barrel/first piston inner wall 50. See FIGS. 7 and 8.

In one embodiment, the groove 34 continues to substantially the distal end of inner barrel/first piston 30, outlining a track ultimately leading to a projection entry point 36. See FIGS. 3, 6, 7. The projection entry point 36 serves as an entrance to the groove 34 for the projection 68, simplifying the assembly process for the syringe, and reducing the cost of construction. Id. In the alternate embodiment, shown in FIG. 8, the second piston 60 with protrusion 68 would be installed into the inner barrel by applying sufficient pressure to temporarily flex the plastic allowing a press-fit construction. See FIGS. 3 and 8.

When the second piston 60 is in the fully extended position, the projection 68 will lie in the radial portion 37 of the groove 34. See FIG. 5. From this position, the second piston 60 may be axially rotated, and the projection 68 will slide along the radial portion 37 of the groove 34. Id. Additionally, the second piston 60 and the inner barrel/first piston 30 are longitudinally locked together, and in this fixed position the two components function collectively as one piston relative to the outer barrel 10. See FIGS. 5 and 15(*a*)-15(*e*). The syringe may then be used in the same manner as a conventional one-chambered syringe.

In yet another embodiment, instead of comprising a track defined by an indented groove on the inner barrel/first piston 30, the syringe comprises a track defined by a raised track 35 outlining the same path previously defined by the groove 34. See FIGS. 2-4, and 16. Correspondingly, the second piston 60 comprises an indentation 69 instead of the projection 68. See FIGS. 2-4. In this configuration raised track 35 fits snugly into indentation 69, thus defining a track for the second piston 60 to follow when in the unlocked position. See FIGS. 2 and 4. In this embodiment, the track need not extend longitudinally the entire length of the inner barrel to accomplish the locking feature.

To ensure the saline does not leak backwards out of the flush chamber, the second piston 60 may additionally comprise breakaway guard 75, which provides a cover over the indentation 69. Id. The breakaway guard 75 may be a layer of plastic that is capable of being punctured by raised track 35 when the operator applies sufficient force. The operator of the syringe will feel the resistance and subsequent release as the breakaway guard is punctured. See FIGS. 2, 4, and 16. The need for this guard may be circumvented by making a rear lip 31 large enough to prevent backward flow of the flush solution. Id. The lip 31 of the inner barrel enables a unidirectional press fit construction (due to the sloped angle of the lip 31) in which the second plunger may be easily slid into the inner barrel, but cannot be easily removed. Id. Thus, the second piston 60 is effectively trapped between the raised track 35 and the lip 31 thus preventing the second piston from moving longitudinally with respect to the inner barrel/first piston when the second piston is in the locked configuration. See FIGS. 15(*a*)-15(*f*).

Other latching mechanisms may be used, and for purposes of this patent, "latching mechanism" refers generically to any structure that can lock and unlock the inner barrel/first piston 30 relative to the second piston 60. See FIG. 1.

One advantage of applicant's device is that the syringe may function as a traditional syringe, independent of the internal flush chamber in the inner barrel/first piston 30. See FIGS. 15(*b*)-15(*e*). Additionally, this syringe may be used to dispense a flush solution without filling the outer chamber with a second liquid or gas.

In operation, the syringe will typically first be in the locked position so medicine withdrawn from a bottle fills the outer chamber 10. See FIG. 15(*a*)-(*d*). When medication is administered directly to a vein, a clinician using a traditional syringe will often confirm that a vein has been pierced by drawing a small amount of blood into the syringe, prior to injection of the medication. This device allows for this normal operation to be performed when the device is in the locked configuration. See FIGS. 15(*b*)-15(*c*).

Figure 5:
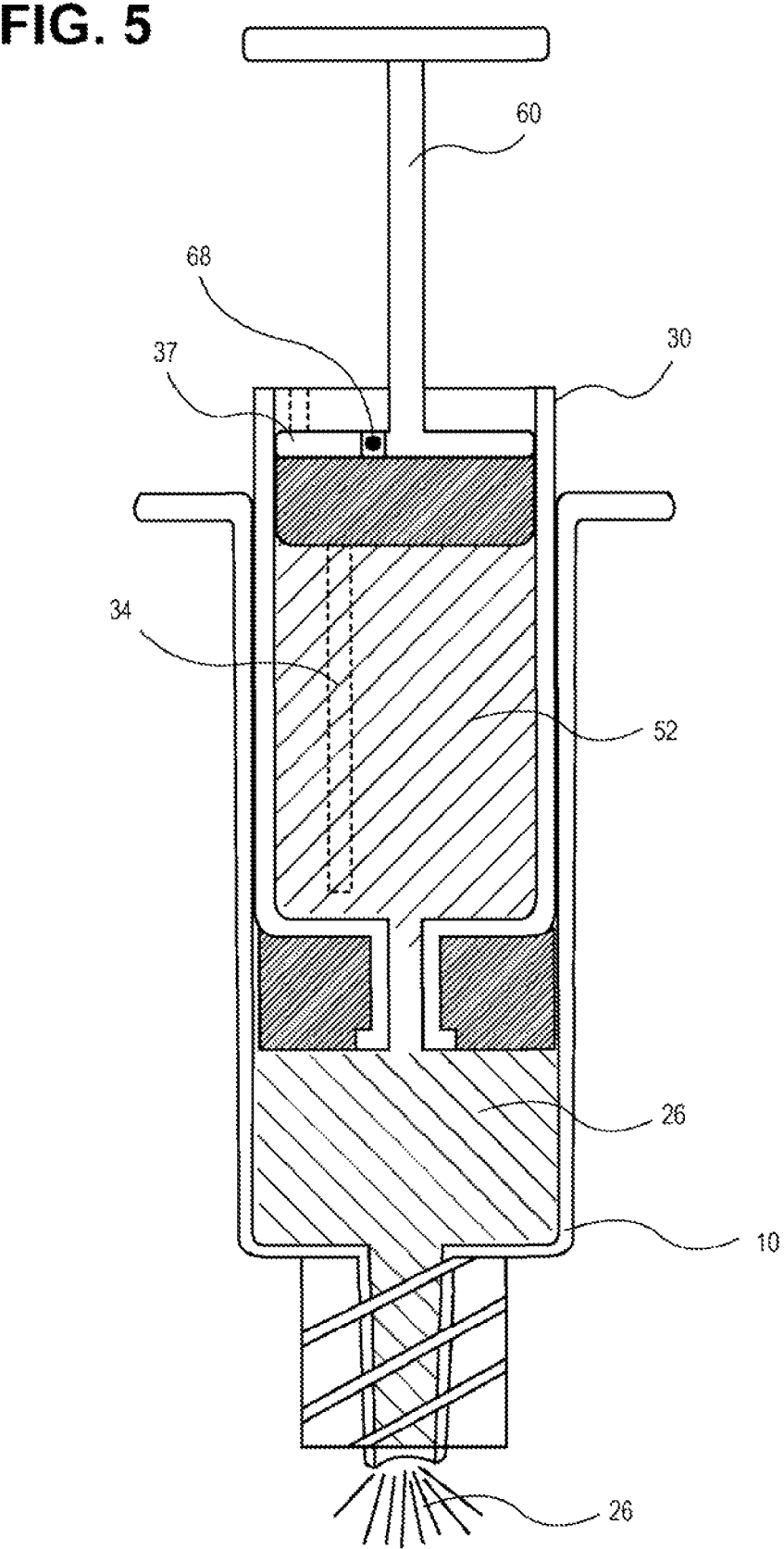
FIG. 5 is a side cross-sectional view of the embodiment depicted in FIG. 1, with the inner barrel/first piston full of a liquid such as a saline solution.
Figure 6:
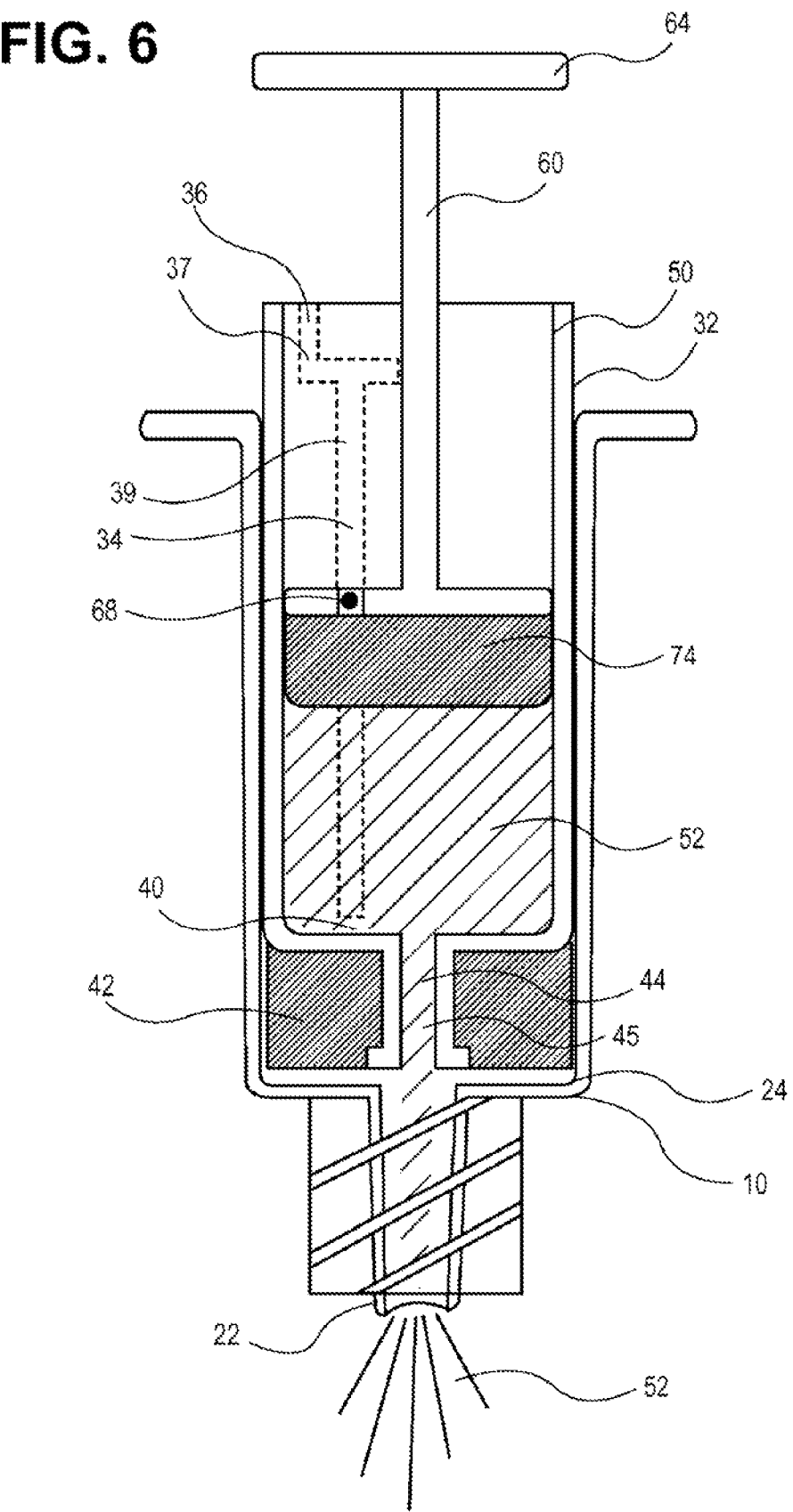
FIG. 6 is a side cross-sectional view of the embodiment depicted in FIG. 1, with the second piston partially depressed, thereby expelling some of the liquid.
Figure 16:
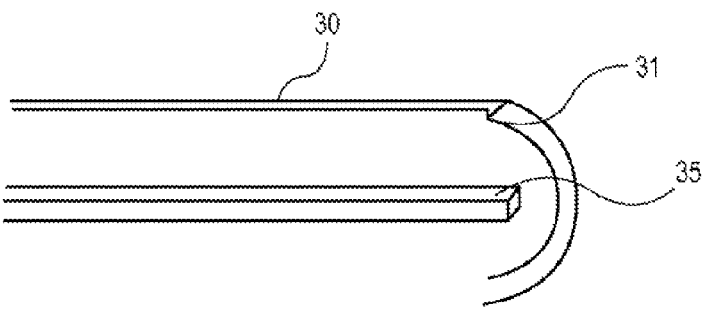
FIG. 16 is a perspective cut away view of the inner barrel/first piston showing the raised track and rear lip.

Because the flushing liquid 52 does not extend through the second conduit 44, it will not mix with fluid drawn into the outer chamber 10. In a separate embodiment, flushing liquid 52 extends only partially through the second conduit 44, but not enough to mix with fluid drawn into outer chamber 10. The two fluids will not come in contact with each other due to basic fluid mechanics. That is, surface tension of the fluid drawn into the outer chamber 10 prevents it from entering the second conduit 44. As shown in FIG. 5, the conduit is coupled between the first chamber and the second chamber and remains at least partially unfilled. The flushing liquid 52 does not move through the second conduit because as it completely fills the inner barrel/first piston 30, the negative pressure created inside the outer barrel 10 when fluid is drawn in, is not great enough to displace the flushing liquid 52 from the inner barrel/first piston 30.

Next, while the syringe is still in the locked configuration, the contents of the outer barrel 10 may be delivered to a patient by depressing the second piston 60. See FIGS. 15(*e*)-15(*f*). After injecting the medication, the operator may axially rotate the second piston 60 until the longitudinal portion 39 of either the groove 34 or the track 35 defines the path of movement. See FIGS. 6 and 15(*f*)-15(*g*). In the embodiments shown in FIG. 2 and FIG. 8 the clinician may confirm this alignment upon feeling that the axial rotation is halted by forward projection 67. In the embodiments shown in FIG. 1 and FIG. 3, a clinician may confirm this alignment by rotating the second piston 60 until an indicating mark on second piston 60 is longitudinally in line with a mark on the inner barrel/first piston 30 or the outer barrel 10. From this position, the second piston 60 may be longitudinally moved down the length of the inner barrel/first piston 30, thereby emptying the contents of the inner barrel/first piston 30 into the outer barrel 10 and then into the catheter. See FIGS. 6 and 15(*f*)-15(*g*).

In the embodiment shown in FIG. 2, after the outer barrel is dispensed the second plunger may be rotated axially until the forward protrusion 67 meets the raised track 35, impeding further rotation. From this position, proper alignment of the track and indentation is assured because the forward protrusion 67 is adjacent to the indentation 69. Next, the operator would depress the second piston 60 a second time, emptying the contents of the inner barrel through second conduit 44. See FIGS. 6 and 15(*f*)-15(*g*). Preferably, at this point in the process, the medication from the outer barrel 10 is already expelled into the intravenous system, and thus the contents of the inner barrel/first piston 30 may be used to flush any remaining medication into the patient.

One skilled in the art will appreciate that the present invention can be practiced by other than the preferred embodiments, which are presented for purposes of illustration and not of limitation.

I claim:

1. A two chambered syringe comprising:

a first chamber comprising an outlet and a movable seal, the first chamber containing a liquid;

a second chamber connected to the first chamber seal and movably disposed with the first chamber movable seal within the first chamber, the second chamber comprising a movable seal, and a conduit coupled between the first chamber and the second chamber and adapted to allow fluid communication between the chambers when the second chamber moveable seal is moved relative to the first chamber moveable seal, the conduit having a reduced cross sectional area relative to a respective cross sectional areas of the first and second chambers, the second chamber containing a solution, wherein the liquid and the solution do not contact each other due to fluid mechanics when disposed within the syringe;

a latching mechanism having a first position in which movement between the first chamber seal and the second chamber seal is prevented to maintain a volume of the second chamber at a fixed volume, and a second position in which movement between the first chamber seal and the second chamber seal is permitted; and a single handle operably connected to the second chamber movable seal to move the first chamber seal within the first chamber when the latching mechanism is in the first position while maintaining the volume of the second chamber at the fixed volume and while expelling the liquid from the first chamber and to move the second chamber seal within the second chamber when the latching mechanism is in the second position allowing for reduction of the volume of the second chamber to expel the solution from the second chamber, and where the conduit remains fluidly coupled between the first and second chamber and the conduit remains at least partially unfilled while expelling the liquid from the first chamber and retaining the solution in the second chamber.

2. The syringe of claim 1 wherein the first chamber comprises a cylinder and the second chamber comprises a cylinder.

3. The syringe of claim 1 wherein the first chamber seal and the second chamber seal are in a first spaced relationship when the latching mechanism is in the first position and there is no other spaced relationship between the first chamber seal and the second chamber seal in which movement between the first and second chambers is prevented.

4. The syringe of claim 3, wherein the solution completely fills the second chamber.

5. The syringe of claim 4 wherein the solution does not extend into the conduit while expelling the liquid from the first chamber and retaining the solution in the second chamber.

6. The syringe of claim 4 wherein the solution only partially extends into the conduit while expelling the liquid from the first chamber and retaining the solution in the second chamber.

7. The syringe of claim 1 wherein the handle is rotatably mounted within the syringe, the handle being movable from a first angular position in which the latching mechanism is in the first position and a second angular position in which the latching mechanism is in the second position.

8. The syringe of claim 1 wherein the latching mechanism further comprises a breakaway guard.

9. The syringe of claim 1, wherein the solution is a saline solution.

10. The syringe of claim 1 wherein the conduit is coaxial with the outlet and is communicable with the outlet to form an unobstructed path from the second chamber through the outlet and conduit.

* * * * *